US006359179B1

(12) United States Patent
Nemeth et al.

(10) Patent No.: US 6,359,179 B1
(45) Date of Patent: Mar. 19, 2002

(54) DIRECT CARBONYLATION OF PARAFFINS USING SOLID STRONG ACID CATALYST

(75) Inventors: Laszlo T. Nemeth, Palatine; Jeffrey C. Bricker, Buffalo Grove, both of IL (US); Jules Rabo, Armonk, NY (US); Ralph D. Gillespie, Gurnee, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/470,631

(22) Filed: Dec. 22, 1999

(51) Int. Cl.$^7$ .............................................. C07C 45/49
(52) U.S. Cl. ...................... 568/387; 568/383; 568/876; 568/881; 568/885; 568/909
(58) Field of Search ................ 568/383, 387, 568/876, 881, 885, 909

(56) References Cited

U.S. PATENT DOCUMENTS

| 2,346,701 A | 4/1944 | Pines et al. ................. 260/488 |
| 2,874,186 A | 2/1959 | Friedman ..................... 260/514 |
| 3,356,720 A | 12/1967 | Mirvisa et al. ............. 260/533 |
| 5,679,867 A | 10/1997 | Bruce et al. ................ 568/428 |

FOREIGN PATENT DOCUMENTS

| WO | 98/50336 | 12/1998 | ............ C07C/45/49 |

OTHER PUBLICATIONS

Luzgin, M.V., *Carbonylation of Isobutane on Sulfated Zirconia*, EuroCat–IV, 4$^{th}$ Europeon Congress on Catalysis, Sep. 1999, pub. European Federation of Catalysis Societies.

Harrison et al, Compendium of Organic Synthetic Methods, p. 111, 1971.*

* cited by examiner

*Primary Examiner*—Sreeni Padmanabhan
(74) *Attorney, Agent, or Firm*—John G. Tolomei; Frank S. Molinaro

(57) ABSTRACT

A process for the direct carbonylation of saturated hydrocarbons has been developed. The process involves contacting the saturated hydrocarbons, which contain at least one primary, secondary or tertiary carbon atom, with carbon monoxide in the presence of a solid strong acid catalyst to produce an oxygenated saturated hydrocarbon. In a specific embodiment isobutane is reacted with carbon monoxide using sulfated zirconia as the catalyst to produce methylisopropyl ketone. The oxygenated hydrocarbon can subsequently be hydrogenated to give a reduced oxygenated saturated hydrocarbon. The hydrogenation can also be done simultaneously with the carbonylation, i.e., reductive carbonylation.

37 Claims, No Drawings

DIRECT CARBONYLATION OF PARAFFINS USING SOLID STRONG ACID CATALYST

FIELD OF THE INVENTION

This invention relates to a process for the carbonylation of a saturated hydrocarbon to give an oxygenated saturated hydrocarbon. The process involves using a solid strong acid catalyst, such as sulfated zirconia, to catalyze the carbon monoxide addition to the saturated hydrocarbon at reaction conditions to form oxygenates. The oxygenate can be subsequently hydrogenated to provide reduced oxygenates, e.g., ketones can be hydrogenated to alcohols. Alternatively, a hydrogenation component can be added to the solid strong acid catalyst such that reductive carbonylation takes place in one step.

BACKGROUND OF THE INVENTION

Industrial chemicals, to a large extent, contain heteroatoms (O, N, S and halide) prepared by processes in which hydrocarbons are converted to organic compounds containing various heteroatoms. Although saturated hydrocarbons such as paraffins and naphthenes are the lowest cost and most readily available hydrocarbons; they are also very stable and thus not very chemically reactive. Therefore, the most common route to preparing various hetero organic compounds has been to first convert the saturated hydrocarbons to olefins and then react the olefins to produce the hetero organic compounds. While this route to many commercial chemicals has been widely adapted in the industry, it is clear that the direct conversion of saturated hydrocarbons to hetero organic chemicals would be preferable since a major step in the process would be eliminated, thereby resulting in substantial economic benefits.

The fundamental problem in converting saturated hydrocarbons directly to hetero organic compounds is the high stability of the C—C and C—H bonds. In view of the high stability of these bonds, attempts to directly convert saturated hydrocarbons to hetero organic molecules have met with few successes. For example U.S. Pat. No. 2,874,186 discloses a process for reacting carbon monoxide with normal paraffins, isoparaffins and naphthenes to produce ketones, acids and esters. The process involves placing the isoparaffin in a reactor with hydrogen fluoride and boron trifluoride (HF/$BF_3$) and carbon monoxide under high pressures. The products, which were obtained from this process, were ketones and carboxylic acids. U.S. Pat. No. 2,346,701 discloses preparing organic oxygen-containing compounds such as ketones and acids by reacting propane with carbon monoxide using an anhydrous aluminum halide catalyst, e.g., aluminum chloride. U.S. Pat. No. 3,356,720 discloses preparing oxygenated organic compounds by reacting saturated hydrocarbons with carbon monoxide using a Freidel-Crafts catalyst and a tertiary alkyl, phenyl alkyl or phenyl carbonyl halide. Both ketones and carboxylic acids are produced. It is also disclosed in WO 98/50336 that branched aliphatic hydrocarbons can be converted to branched aliphatic ketones by reacting the hydrocarbons with carbon monoxide at high pressures and super acidic conditions. The super acidic conditions are produced by the combination of a protic acid such as HF and a Lewis acid such as $BF_3$. The reaction is carried out at temperatures of about 0° C. to about 35° C. and pressures of about 10 to 200 atmospheres. Both of these references use a homogeneous liquid system in which the catalyst is a highly corrosive compound. Additionally, means for separating the desired product from the reaction mixture is not disclosed and is anticipated to be very difficult.

At the EuroCat-IV meeting in Rimini, Italy, Sep. 5–10, 1999, M. V. Luzgin and A. G. Stepanov reported that isobutane can be carbonylated with carbon monoxide on sulfated zirconia at 70–150° C. They adsorbed CO and isobutane onto sulfated zirconia and obtained the $^{13}$C NMR spectrum of the catalyst-product complex, which showed the presence of methylisopropyl ketone or pivalic acid. Finally, U.S. Pat. No. 5,679,867 discloses that arylene compounds such as toluene can be carbonylated with carbon monoxide over a solid acid catalyst such as promoted sulfated zirconia to give tolualdehyde.

In contrast to the above references, applicants have developed a process by which saturated hydrocarbons are reacted with carbon monoxide over a solid strong acid catalyst such as sulfated zirconia to give a high yield of an oxygenated saturated hydrocarbon. By oxygenated is meant an oxygen containing saturated hydrocarbon. A specific example is the carbonylation of isobutane to methylisopropyl ketone over sulfated zirconia. Hydrogenation of the oxygenate, e.g., ketone can simultaneously occur by adding a hydrogenation component to the solid catalyst and a reducing agent such as hydrogen. Alternatively, hydrogenation can be carried out in a separate step and reactor.

SUMMARY OF THE INVENTION

This invention relates to the carbonylation of saturated hydrocarbons to provide an oxygenated saturated hydrocarbon. Accordingly, one embodiment of the invention is a process for preparing an oxygenated saturated hydrocarbon comprising contacting a saturated hydrocarbon with carbon monoxide and a solid strong acid catalyst at reaction conditions to provide an oxygenated saturated hydrocarbon product.

Another embodiment of the invention is the reductive carbonylation of saturated hydrocarbons comprising contacting the saturated hydrocarbon with carbon monoxide and a hydrogen source in the presence of a strong acid catalyst containing a hydrogenation catalyst component at reductive carbonylation conditions to provide a reduced oxygenated saturated hydrocarbon product.

These and other objects and embodiments will become clearer after a detailed description of the invention.

DETAILED DESCRIPTION OF THE INVENTION

Generally, the present invention relates to the direct carbonylation of saturated hydrocarbons to form the corresponding oxygenated saturated hydrocarbons. As stated, by oxygenate is meant an oxygen containing saturated hydrocarbon, with saturated referring to the hydrocarbon portion of the molecule. Non-limiting examples of these oxygenates are ketones aldehydes and acids. Without wishing to be bound by any particular theory, the reaction pathway by which direct carbonylation to ketones takes place involves the formation of a carbocation species, i.e., a carbenium or carbonium ion which is then reacted, i.e., intercepted, by carbon monoxide molecules forming a relatively stable oxycarbocation. The oxycarbocation undergoes further molecular rearrangement involving an intramolecular hydrogen transfer, i.e., hydride shift, to produce an aldehyde, and an intramolecular methyl shift to convert the aldehyde to the more stable ketone.

Accordingly, those saturated hydrocarbon compounds, which can be used in the present invention, are any of those that can form a carbocation at reaction conditions. The hydrocarbons, which meet these criteria, are any of those which contain at least one of a primary, secondary or tertiary carbon as described in standard organic chemistry texts. Preferred hydrocarbons are those which contain one or more tertiary carbon. For the purpose of this invention, the hydrocarbons which meet these criteria are the saturated hydrocarbons which include alkanes and cyclic alkanes. Although the number of carbon atoms which the saturated hydrocarbons can have is not a critical aspect of this invention, for practical purposes those having 1 to 30 carbon atoms are usually used and thus are preferred.

Included in the general category of alkanes are straight chain alkanes, single and multiple branched alkanes. Cyclic alkanes include cyclic alkanes having one or more alkyl groups attached to the ring. Especially preferred alkanes are the branched alkanes (branched such that they contain one or more tertiary carbon) having from 4 to about 30 carbon atoms. Specific examples of branched alkanes include, but are not limited to, isobutane, isooctane, methylcyclopentane, methylcyclohexane, 2,3-dimethylbutane and 2-methylundecane. Further, mixtures of any of the $C_4$–$C_{30}$ alkanes can be used in the process and indeed mixtures can lead to very useful products. Examples of these mixtures include, but are not limited to, mixtures of butane and isobutane; mixtures of $C_6$ isomers including 2,2-dimethyl butane, 2,3 dimethyl butane, 2-methyl pentane, 3-methyl pentane and n-hexanes; detergent range isoparaffins which usually include $C_{10}$ to $C_{16}$ isoparaffins; etc. It should be pointed out that the initial hydrocarbon feed, in the presence of the strong acid catalyst at reaction conditions, can undergo isomerization from unbranched to branched (tertiary carbon) hydrocarbons. Thus, the preferred hydrocarbons can be generated in situ.

A solid strong acid catalyst is required to react the hydrocarbon with carbon monoxide. Liquid acids whose strength is greater than sulfuric acid have been termed "superacids". A number of liquid super acids are known in the literature including substituted protic acids, e.g., trifluoromethyl substituted $H_2SO_4$, triflic acid and protic acids activated by Lewis acids (HF plus $BF_3$). While determination of the acid strength of liquid super acids is relatively straightforward, the exact acid strength of a solid strong acid is difficult to directly measure with any precision because of the less defined nature of the surface state of solids relative to the fully solvated molecules found in liquids. Accordingly, there is no generally applicable correlation between liquid super acids and solid strong acids such that if a liquid super acid is found to catalyze a reaction, there is no corresponding solid strong acid which one can automatically choose to carry out the same reaction. Therefore, as will be used in this specification, "solid strong acids" are those that have an acid strength greater than sulfonic acid resins such as Amberlyst®-15. Additionally, since there is disagreement in the literature whether some of these solid acids are "superacids" only the term solid strong acid as defined above will be used herein.

Another way to define a solid strong acid is a solid comprising of interacting protic and Lewis acid sites. Thus, solid strong acids can be a combination of a Bronsted (protonic) acid and a Lewis acid component. In other cases, the Bronsted and Lewis acid components are not readily identified or present as distinct species, yet they meet the above criteria.

Examples of the solid acids which fall within the bounds of this invention include but are not limited to sulfated metal oxides (especially sulfated zirconia), fluorocarbon sulfonates (—$(CF_2)_n$—$SO_3H$) in combination with supports (e.g. metal oxides and carbon), heteropolyacids, halides of Ta, Sb, Ga and B in combination with halogenated metal oxides, sulfated zeolites, halides of Ta, Sb, Ga and B in combination with fluorosulfonic acid resins, Nafion® and substituted Nafion®. Nafion® is a perfluorinated copolymer of tetrafluoro-ethylene and perfluoro-3,6 dioxa-4methyl-7-octenesulfonic acid. Nafion® can be substituted by treating with a Lewis acid including but not limited to $AlCl_3$, $TaF_5$, $SbF_5$. It should be pointed out that metal oxides as used herein include both single component oxides or multi-component oxides, i.e., mixed metal oxides. Single component metal oxides include but are not limited to aluminas, silicas, zirconia, titania and mixtures thereof. The mixed metal oxides can be either physical mixtures or preferably structurally connected. Examples of mixed metal oxides include but are not limited to Zr—Ti, W—Zr, Ti—Cu, Ti—Zn, Ti—Si, Al—Zr, Fe—Zr and Ti—Mn oxides. Specific examples of the solid strong acids include, but are not limited to, sulfated zirconia, sulfated titania, sulfated tungsten oxide, $BF_3$ on fluorinated alumina, aluminum chloride on chlorinated alumina, $TaF_5$ in combination with Nafion®, $H_3PW_{10}O_{40}$, $Cs_{2.5}H_{0.5}PW_{12}O_{40}$, $H_4SiW_{12}O_{40}$, etc.

The synthesis of the above named solid strong acids can be carried out using conventional techniques known in the art and will be repeated here only for completeness. For example, there are numerous methods of preparing sulfated zirconia, which are reviewed in "Catalysis Review"—Sci. Eng. 38 (3), 329–412, 1996. Generally, the method involves hydrolyzing a zirconium salt, such as $ZrOCl_2$ or $ZrO(NO_3)_2$ with aqueous ammonia to produce zirconium hydroxide. Next the zirconium hydroxide is treated with dilute sulfuric acid or $(NH_4)_2SO_4$ solution followed by drying. The resultant sulfated zirconium hydroxide is calcined in air at 550° C. to about 650° C. to generate strong acidity. Aluminum chloride on alumina or chlorinated alumina is also a well-known solid strong acid, which can be synthesized by vapor deposition of sublimed aluminum chloride on chlorinated alumina at high temperatures. Chlorinated alumina is in turn prepared by treatment of gamma alumina with hydrochloric acid.

Promoters can also be incorporated with the solid strong acid in order to increase catalyst activity for specific reactions. Thus, sulfated zirconia can be promoted by elements such as V, Cr, Co, Ni, Fe, Cu, Mo, Mn, W, the lanthanide elements and mixtures thereof. Preferred promoters are Fe, Mn, Ce, Cr, Ni and W. These promoters can be incorporated or combined with the solid acid catalyst by means well known in the art such as impregnation, spray drying, coprecipitation etc. Specific examples are provided in the examples. The final promoter may be in the form of the metal oxide, reduced metal or become chemically part of the strong acid structure.

The solid strong acid catalyst can also have a hydrogenation catalyst component in order to reduce the oxygenates, e.g., ketones to reduced oxygenates, for example alcohols. In this case the process is called reductive carbonylation. Hydrogenation catalyst components include but are not limited to Group VIII metals of the Periodic Table, molybdenum, tungsten and mixtures thereof. Preferred hydrogenation components are the platinum group metals. The platinum group metals are platinum, palladium, rhodium, iridium, ruthenium and osmium. Preferred platinum group metals are platinum and palladium. The hydrogenation catalyst component is present in an amount from about 1 to about 10 wt. % as the metal. Accordingly, these hydrogenation components are incorporated or combined with the solid acid catalyst by the same means as the promoters described above. The hydrogenation component and promoter can be added in any order including simultaneously although not necessarily with equivalent results. The hydrogenation is carried out with a hydrogen containing gas.

The carbonylation reaction is conducted by contacting the desired saturated hydrocarbon feed and carbon monoxide with the solid strong acid catalyst. The three components can be mixed in any order although not necessarily with equivalent results. The process can be carried out in either a batch process or a continuous flow process. In a batch process one way of carrying out the process involves placing the catalyst in an autoclave followed by the addition of the desired hydrocarbon and finally, pressuring with carbon monoxide. Of course the reverse addition can also be done, i.e., carbon monoxide first and then hydrocarbon. The pressure of carbon monoxide can vary considerably but usually, is between 345 kPa to about 27,580 kPa (50 to 4,000 psig). The autoclave is then heated to a temperature of about 20° C. to about 200° C. and preferably from about 50° C. to about 150° C. for a time sufficient to form the desired oxygenated hydrocarbon. The time varies from about 1 min. to about 20 hrs. After the desired time has elapsed, the autoclave is vented. Depending on the choice of hydrocarbon, conditions and catalyst, the product may be in solution or chemically attached to the catalyst.

As used in the present application, attached includes either physical adsorption or chemical e.g., ionic complex. If the product is attached to the catalyst, then the catalyst is treated in order to remove the product attached to the catalyst. The catalyst can be heated such that the product is thermally desorbed. Alternatively, a suitable solvent or chemical displacing agent can be used. Examples of these include but are not limited to water, steam, and organic solvents such as but not limited to methanol, ethanol, acetonitrile, hexamethylbenzene, etc. Polar solvents are preferred.

As stated, the product obtained from the carbonylation of saturated hydrocarbon with carbon monoxide is an oxygenated saturated hydrocarbon. The major product will be a ketone, with other products being carboxylic acids and aldehydes. If the alkane or cyclic alkane has more than one tertiary carbon, e.g., di, tri, or poly tertiary carbons, then di, tri or poly oxygenated saturated hydrocarbons can be obtained. Of course, as stated above the hydrocarbon feed can be a mixture of species and thus a mixture of mono, di, or poly oxygenated products can be obtained.

In a continuous mode, the catalyst may be employed as a fixed bed over which are flowed a mixture of carbon monoxide and the chosen saturated hydrocarbon(s). In this case, the reaction mixture is flowed over the catalyst at a space velocity of about 0.01 to about 10 $hr^{-1}$, while maintaining a pressure of about 345 kPa to about 27,580 kPa (50 to about 4,000 psig) at a temperature of about 20° C. to about 200° C.

If the solid strong acid also contains a hydrogenation component, then instead of adding only carbon monoxide, a mixture of carbon monoxide and hydrogen is used. The ratio of $CO/H_2$ can vary considerably but usually is from about 1 to about 90 and preferably from about 0.5 to about 2. Further, the ratio of $H_2$ to oxygenated hydrocarbon varies from about 1 to about 10. The carbon monoxide and hydrogen can be introduced separately, premixed and introduced as one gas or snygas can be used. It should be pointed out that for $C_1$ to $C_3$ hydrocarbons, i.e., methane, ethane and propane, although carbonylation can be carried out (see example 11) reductive carbonylation is preferred in order to drive the carbonylation reaction. In this case one obtains reduced oxygenated saturated hydrocarbons which are mostly alcohols.

Alternatively, hydrogenation of the oxygenated hydrocarbon can be carried out in a separate step. In this case, the oxygenated hydrocarbon is reacted with a hydrogen containing gas in the presence of a hydrogenation catalyst to give the corresponding reduced oxygenated hydrocarbon. Again, the process can be carried out in a batch or continuous mode with continuous mode being preferred. Hydrogenation conditions include a temperature of about 20° C. to about 200° C., a pressure of about 345 kPa to about 27,580 kPa (50 to about 4,000 psig) and a liquid hourly space velocity of about 0.5 to about 10 $hr^{-1}$. In a batch mode the contact time varies from about 1 minute to about 5 hrs.

The hydrogenation catalyst comprises a hydrogenation component dispersed on a suitable support. The hydrogenation components are the same as enumerated above. The support can be any support, which is inert to the reactants and products and has a sufficient surface area in order to disperse the hydrogenation component thereon. The surface area should be at least 5 $m^2/g$. Specific examples include, but are not limited to, metal oxides, organic polymers, halogenated metal oxides, carbon and fluorinated carbon. These hydrogenation catalysts are prepared by conventional techniques in which one or more hydrogenation metal compounds are dissolved in a suitable solvent and then contacted with the support. Contacting can be done by impregnation, spray drying, etc. As stated above, the final form of the hydrogenation component can be a metal, metal oxide or a metal compound. Finally, the concentration of the hydrogenation component can vary from about 1 to about 10 wt. % of the catalyst as the metal.

The oxygenated (or reduced oxygenated) hydrocarbons of this invention have various uses as solvents, gasoline additives, surfactants, monomers for polymers, etc.

The following examples are set forth to illustrate the invention. It is to be understood that the examples are only by way of illustration and are not intended as an undue limitation on the broad scope of the invention as set forth in the appended claims.

EXAMPLE 1

In a container, 100 g of gamma alumina was heated to 550° C. in flowing nitrogen and then was treated with dry HCl gas for 2 hours. Next the chlorinated alumina was saturated with sublimed aluminum trichloride for 2 hrs. at 550° using dry nitrogen as the carrier gas.

A Parr reactor was loaded in air, with 25 g of the catalyst from the previous paragraph. To this reactor, there were added 200 ml of liquid isobutane. Next, 170 µL of t-butyl chloride and 20 µL of water were added and the autoclave pressurized with dry carbon monoxide to 850 psig. The autoclave was heated up to 50° C. for two hours at which point the autoclave was cooled to room temperature and the carbon monoxide and the isobutane were vented. The contents of the autoclave were treated with 50 ml of water and sodium bicarbonate was added to neutralize the solution to a pH of 7. Finally, the aqueous phase with extracted with diethyl ether and the ether phase was analyzed by gas chromatography. Based on an external methyl-isopropyl ketone standard it was calculated that 0.63 gms of methyl isopropyl ketone was produced.

EXAMPLE 2

A Parr reactor was loaded in a dry box with 25 g of a catalyst comprising aluminum chloride sublimed onto chlorinated alumina, prepared per example 1, to which there were added 200 ml of liquid isobutane. Next, the autoclave was pressurized to 1000 psig with 100 ppm of HCl in nitrogen. The catalyst adsorbed the HCl and the nitrogen was vented. The autoclave was now pressurized with dry carbon monoxide to 850 psig and then heated to 50° C. for 2 hours. At the end of the 2 hours the autoclave was cooled to room temperature and the carbon monoxide and isobutane was vented. The contents of the autoclave were treated with 50 ml of water followed by the addition of sodium bicarbonate to neutralize the aqueous solution to a pH of 7. The aqueous phase was separated from the solid phase and treated with diethyl ether. The ether phase was now analyzed by gas chromatography as in example 1, which gave a calculated yield of 0.87 gms of methylisopropyl ketone.

EXAMPLE 3

Hydrous zirconium oxide was prepared by hydrolyzing $ZrOCl_2.8H_2O$ with a 25 wt. % aqueous ammonia solution with vigorous stirring at room temperature. The product was isolated, washed and dried at 170° C. overnight. This product was now impregnated with ammonium sulfate, dried overnight and calcined at 650° C. for 3 hours.

A Parr reactor was loaded, in air, with 30 g of the sulfated zirconia from the previous paragraph and then charged with 200 ml of liquid isobutane and pressurized with dry carbon monoxide to 1000 psig. The autoclave was heated to 100° C. for 12 hours and then cooled down to room temperature. The carbon monoxide and isobutane were vented and the catalyst was treated with 50 ml of water at room temperature. The aqueous phase was separated from the solid phase and extracted with diethylether and the ether phase analyzed by GC. Using the same analysis technique as in example 1, the product was calculated to be 0.14 gm of pivalic acid and 0.007 gm of methylisopropyl ketone. The prevalence of pivalic acid is consistent with the fact that some water was present in the reaction.

EXAMPLE 4

A Parr reactor was loaded, in a dry box, with 30 g of pre-dried sulfated zirconia. To this reactor there were added 200 ml of liquid isobutane and the reactor was pressured with dry carbon monoxide to 1500 psig. The autoclave was heated to 100° C. for 12 hours and then cooled to room temperature at which point the carbon monoxide and isobutane were vented and the catalyst was treated with 50 ml of water at room temperature. The aqueous phase was separated from the solid catalyst and extracted with diethylether and the ether phase was analyzed by GC. Using the same standard as in example 1, it was calculated that 0.043 g of methylisopropyl ketone was produced.

EXAMPLE 5

The spent sulfated zirconia catalyst of example 4 was calcined at 400° C. and then cooled to room temperature in flowing dry nitrogen. A Parr reactor was loaded in a dry box with 18 g of the calcined sulfated zirconia and charged with 200 ml of liquid isobutane. Next the autoclave was pressurized with dry carbon monoxide to 1500 psig and the autoclave heated to 100° C. for 12 hours after which the autoclave was cooled down to room temperature. The carbon monoxide and isobutane were vented and the catalyst was treated with 50 ml of water at room temperature. The aqueous phase was separated with diethylether, which was analyzed as in example 1. It was calculated that 0.0072 grams of methylisopropyl ketone was produced.

EXAMPLE 6

A catalyst comprising Pt/Mn/sulfated zirconia was prepared by impregnating hydrous zirconium hydroxide with manganese nitrate followed by drying at 120° for 10 hours, Next the solid was impregnated with ammonium sulfate, dried at 120° C. for 10 hours, calcined at 150° C. for 2 hours, 300° C. for 2 hours and 650° C. for 2 hours. Finally, the Mn/sulfated zirconia was impregnated with chloroplatinic acid, dried at 120° C. for 10 hours and calcined at 600° C. for 2 hours.

A Parr reactor was loaded, in a dry box, with 30 g of pre-dried Pt/Mn/sulfated zirconia prepared above. To this reactor there were added 200 ml of liquid isobutane and the reactor was pressured with dry carbon monoxide to 1500 psig. The autoclave was heated to 80° C. for 12 hours and then cooled to room temperature at which point the carbon monoxide and isobutane were vented and the catalyst was treated with 50 ml of water at room temperature. The aqueous phase was separated from the solid catalyst and extracted with diethylether and the ether phase was analyzed by GC. Using the same standard as in example 1, it was calculated that 0.019 g of methylisopropyl ketone was produced.

EXAMPLE 7

A Pt/Fe/Mn sulfated zirconia catalyst was prepared as per example 6 except that iron nitrate was added to the manganese nitrate solution.

A Parr reactor was loaded, in a dry box, with 30 g of pre-dried Pt/Fe/Mn/sulfated zirconia prepared as described above. To this reactor there were added 200 ml of liquid isobutane and the reactor was pressurized with dry carbon monoxide to 1500 psig. The autoclave was heated to 100° C. for 12 hours and then cooled to room temperature at which point the carbon monoxide and isobutane were vented and the catalyst was treated with 50 ml of water at room temperature. The aqueous phase was separated from the solid catalyst and extracted with diethylether and the ether phase was analyzed by GC. Using the same standard as in example 1, it was calculated that 0.0154 g of methylisopropyl ketone and 0.0051 g pivalic acid were produced.

EXAMPLE 8

A solution containing 0.08 mol/l of $H_3 PW_{12}O_{40}$ was titrated with an aqueous solution of 0.25 mol/l of $Cs_2CO_3$. The suspension was filtered, the solid washed and the solid material dried at 120° C. and then calcined at 300° C. to give a product having an empirical formula of $Cs_{2.5}H_{0.5}PW_{12}O_{40}$.

A Parr reactor was loaded in a dry box with 40 g of the $Cs_{2.5}H_{0.5}PW_{12}O_{40}$ prepared above and charged with 200 ml of liquid isobutane. Next the autoclave was pressurized with dry carbon monoxide to 1500 psig and the autoclave heated to 110° C. for 12 hours after which the autoclave was cooled down to room temperature. The carbon monoxide and isobutane were vented and the catalyst was treated with 50 ml of water at room temperature. The aqueous phase was separated with diethylether, which was analyzed by GC-MS. Small amounts of 2,2-dimethyl-propanoic acid and 2-methyl-butanoic acid were identified by the MS spectrum.

EXAMPLE 9

Fluorinated alumina (50 g) prepared by treating alumina with ammonium fluoride was loaded into a quartz reactor and pretreated at 550° C. for 2 hrs in flowing nitrogen. The reactor temperature was lowered to 250° C., the nitrogen feed switched to $BF_3$ and treated with the $BF_3$ vapor for 2 hours.

A Parr reactor was loaded in a dry box with 40 g of the $BF_3$ on F-Alumina prepared above and charged with 200 ml of liquid isobutane. Next the autoclave was pressurized with dry carbon monoxide to 1500 psig and the autoclave heated to 100° C. for 12 hours after which the autoclave was cooled down to room temperature. The carbon monoxide and isobutane were vented and the catalyst was treated with 50 ml of water at room temperature. The aqueous phase was separated with diethylether, which was analyzed by GC and GC-MS. The products were identified as 2,2-dimethyl-proponoic acid and 2-methyl-butanoic acid by GC-MS. Based on GC peak area it was calculated that 0.0275 g 2,2-dimethyl-propionic acid was produced.

EXAMPLE 10

In a glass liner there were added 50 g of methyl-isopropylketone (MIPK) in 100 g of n-pentane. To this there were added 5 g of a Pd on carbon catalyst. The liner was placed in a rotating autoclave and pressurized with pure hydrogen to 1500 psig. The autoclave was heated to 100° C. for 6 hours and then cooled to room temperature. The liquid was analyzed by gas chromatography which showed the conversion of MIPK to be 95.5% and the selectivity to 3-methyl-2-butanol was 99.4%.

EXAMPLE 11

A $SbF_5$ on fluorinated graphite was prepared by taking 25 g of fluorinated graphite powder with an empirical formula of $CF_{0.8}$, which was heated to 150° C. in nitrogen and transferred to a container in a dry box. To the fluorinate graphite there were added 6.25 g of $SbF_5$ dissolved in 30 g of 1,1,2-trichlorofluoroethane. The solvent was removed using dry nitrogen and heated to 100° C. for two hours.

In a Teflon® lined autoclave there were added 10 g of the above catalyst and then the autoclave was pressurized up to 100 psig with methane and then up to 1000 psig with carbon monoxide. The autoclave was then heated to 80° C. for 5 hours. After 5 hours, the autoclave was cooled to room temperature, depressurized and the catalyst treated with water and filtered. The solid catalyst was extracted with methanol and analyzed which showed the presence of 0.004 g acetaldehyde and 0.002 g of acetic acid.

We claim as our invention:

1. A process for preparing an oxygenated saturated hydrocarbon comprising contacting a saturated hydrocarbon with carbon monoxide and a solid strong acid catalyst at reaction conditions to provide an oxygenated saturated hydrocarbon.

2. The process of claim 1 where the saturated hydrocarbon is at least one saturated hydrocarbon having from 1 to 30 carbon atoms.

3. The process of claim 2 where the saturated hydrocarbon is selected from the group consisting of alkanes, cycloalkanes and mixtures thereof.

4. The process of claim 3 where the alkanes are branched alkanes which contain at least one tertiary carbon.

5. The process of claim 1 where the oxygenated hydrocarbon is a ketone.

6. The process of claim 3 where the alkanes are selected from the group consisting of isobutane, isooctane, 2,3-dimethylbutane, 2,2-dimethylbutane, 2-methylpentane, 3-methyl pentane, $C_{10}$ to $C_{16}$ isoparaffins and mixtures thereof.

7. The process of claim 1 where the saturated hydrocarbon contains at least two tertiary carbons which provide an oxygenated saturated hydrocarbon containing at least two oxygenated carbons.

8. The process of claim 1 where the process is carried out in a batch mode and the reaction conditions include a pressure of about 345 to about 27,580 kPa (50 to about 4,000 psig), a temperature of about 20° C. to about 200° C. and a contact time of about 1 min to about 20 hours.

9. The process of claim 1 where the process is carried out in a continuous mode and the reaction conditions include a pressure of about 345 to about 27,580 kPa (50 to about 4,000 psig), a temperature of about 20° C. to about 200° C., and a space velocity of about 0.01 to about 10 $hr^{-1}$.

10. The process of claim 1 where the solid strong acid catalyst is selected from the group consisting of sulfated metal oxides, heteropolyacids, sulfated zeolites, fluorocarbon sulfonates in combination with supports, halides of Ta, Sb, Ga and B in combination with fluorosulfonic acid resins or metal oxides, Nafion® and substituted Nafion®.

11. The process of claim 10 where the solid strong acid catalyst is sulfated zirconia.

12. The process of claim 10 where the solid acid catalyst is promoted with an element selected from V, Cr, Co, Ni, Fe, Cu, Mo, Mn, W, the lanthanide elements and mixtures thereof.

13. The process of claim 1 further comprising contacting the oxygenated saturated hydrocarbon with hydrogen and a hydrogenation catalyst at hydrogenation conditions to convert the oxygenated saturated hydrocarbon to a reduced oxygenated saturated hydrocarbon.

14. The process of claim 13 where the hydrogenation is carried out in a continuous mode and the hydrogenation conditions include a $H_2$/oxygenated hydrocarbon ratio of about 1 to about 10, a pressure of about 345 to about 27,580 kPa, a temperature of about 20° C. to about 200° C. and a liquid hourly space velocity of about 0.5 to about 10 $hr^{-1}$.

15. The process of claim 13 where the hydrogenation catalyst comprises a hydrogenation component selected from the group consisting of a Group VIII metal component, a tungsten component, a molybdenum component and mixtures thereof dispersed on a support.

16. The process of claim 15 where the hydrogenation catalyst comprises palladium on carbon.

17. The process of claim 1 where the oxygenated saturated hydrocarbon is chemically attached to the solid strong acid catalyst.

18. The process of claim 17 where the oxygenated saturated hydrocarbon is thermally desorbed.

19. The process of claim 17 where the oxygenated saturated hydrocarbon is removed from the catalyst by a solvent or chemical displacing agent.

20. The process of claim 19 where the solvent is selected from the group consisting of methanol, ethanol, acetonitrile and hexamethylbenzene.

21. A process for the reductive carbonylation of a saturated hydrocarbon comprising contacting the saturated hydrocarbon with carbon monoxide and hydrogen in the presence of a strong acid catalyst containing a hydrogenation component at reductive carbonylation conditions to provide a reduced oxygenated saturated hydrocarbon.

22. The process of claim 21 where the saturated hydrocarbon is at least one saturated hydrocarbon having from 1 to 30 carbon atoms.

23. The process of claim 22 where the saturated hydrocarbon is selected from the group consisting of alkanes, cycloalkanes and mixtures thereof.

24. The process of claim 23 where the alkanes are branched alkanes which contain at least one tertiary carbon.

25. The process of claim 21 where the reduced oxygenated saturated hydrocarbon is an alcohol.

26. The process of claim 23 where the alkanes are selected from the group consisting of isobutane, isooctane, 2,3-dimethylbutane, 2,2-dimethylbutane, 2-methylpentane, 3-methyl pentane, $C_{10}$ to $C_{16}$ isoparaffins and mixtures thereof.

27. The process of claim 21 where the process is carried out in a batch mode and the reaction conditions include a pressure of about 345 to about 27,580 kPa a temperature of about 20° C. to about 200° C. and a contact time of about 1 min. to about 20 hours.

28. The process of claim 21 where the process is carried out in a continuous mode and the reaction conditions include a pressure of about 345 to about 27,580 kPa (50 to about 4,000 psig), a temperature of about 20° C. to about 200° C., a contact time of about 1 min to about 20 hours and a space velocity of about 0.01 to about 10 $hr^{-1}$.

29. The process of claim 21 where the solid strong acid catalyst is selected from the group consisting of sulfated metal oxides, heteropolyacids, sulfated zeolites, fluorocarbon sulfonates in combination with supports, halides of Ta, Sb, Ga and B in combination with fluorosulfonic acid resins or metal oxides, Nafion® and substituted Nafion®.

30. The process of claim 29 where the solid strong acid catalyst is sulfated zirconia.

31. The process of claim 29 where the solid strong acid catalyst is promoted with an element selected from V, Cr, Co, Ni, Fe, Cu, Mo, Mn, W, the lanthanide elements and mixtures thereof.

32. The process of claim 21 where the hydrogenation component is selected from the group consisting of a tungsten component, a molybdenum component, a Group VIII metal component and mixtures thereof.

33. The process of claim 32 where the hydrogenation component is palladium.

34. The process of claim 21 where the ratio of CO to $H_2$ varies from about 1 to about 90.

35. The process of claim 21 where the oxygenated saturated hydrocarbon is chemically attached to the solid strong acid catalyst.

36. The process of claim 35 where the oxygenated saturated hydrocarbon is thermally desorbed.

37. The process of claim 17 where the oxygenated saturated hydrocarbon is removed from the catalyst by a solvent or chemical displacing agent.

* * * * *